US008853626B2

(12) United States Patent
Hiraoka et al.

(10) Patent No.: US 8,853,626 B2
(45) Date of Patent: Oct. 7, 2014

(54) IONIZATION APPARATUS AND IONIZATION ANALYSIS APPARATUS

(71) Applicant: University of Yamanashi, Kofu (JP)

(72) Inventors: Kenzo Hiraoka, Kofu (JP); Lee Chuin Chen, Kofu (JP)

(73) Assignee: University of Yamanashi, Yamanashi (JP)

( * ) Notice: Subject to any disclaimer, the term of this patent is extended or adjusted under 35 U.S.C. 154(b) by 0 days.

(21) Appl. No.: 14/172,400

(22) Filed: Feb. 4, 2014

(65) Prior Publication Data

US 2014/0151550 A1 Jun. 5, 2014

Related U.S. Application Data

(63) Continuation-in-part of application No. 13/566,463, filed on Aug. 3, 2012, which is a continuation-in-part of application No. PCT/JP2011/053314, filed on Feb. 19, 2011.

(30) Foreign Application Priority Data

Feb. 12, 2010 (JP) ................................ 2010-029157

(51) Int. Cl.
| | |
|---|---|
| H01J 49/10 | (2006.01) |
| H01J 49/00 | (2006.01) |
| H01J 27/00 | (2006.01) |
| G01N 27/68 | (2006.01) |
| H01J 49/14 | (2006.01) |
| H05H 1/24 | (2006.01) |

(52) U.S. Cl.
CPC ........ *H01J 49/10* (2013.01); *H05H 2001/2412* (2013.01); *H05H 1/2406* (2013.01); *H05H 2001/2443* (2013.01); *G01N 27/68* (2013.01); *H01J 49/145* (2013.01); *H01J 49/105* (2013.01)
USPC ........................................... 250/288; 250/281

(58) Field of Classification Search
USPC ........................... 250/281, 282, 288, 423, 424
See application file for complete search history.

(56) References Cited

U.S. PATENT DOCUMENTS 5,669,904 A * 9/1997 Platt et al. ........................ 606/27
5,889,199 A * 3/1999 Wong et al. ...................... 73/40

(Continued)

FOREIGN PATENT DOCUMENTS

| WO | 2008/153199 A1 | 12/2008 |
| WO | 2009/157312 A1 | 12/2009 |

OTHER PUBLICATIONS

Chen et al., Development of ambient sampling chemi/chemical ion source with dielectric barrier discharge, Journal of Mass Spectrometry, vol. 45, pp. 861-869, 2010.

(Continued)

*Primary Examiner* — Bernard E Souw

(74) *Attorney, Agent, or Firm* — Morgan, Lewis & Bockius LLP

(57) ABSTRACT

A sampling nozzle 21, an ion supply tube 31 leading to an analysis apparatus 50 and a barrier discharge tube 11 are connected to first, second and third ends, respectively, of a T-shaped tube 41 having three connecting ports, and the central portion of the T-shaped tube is an ionization chamber SP. The ionization chamber SP is a closed space, and ions generated therein are introduced to the analysis apparatus 50 through the ion supply tube 31. As a result, almost all of the ions are introduced into the interior of the analysis apparatus.

20 Claims, 9 Drawing Sheets

(56) References Cited

U.S. PATENT DOCUMENTS

| | | | |
|---|---|---|---|
| 6,107,626 A * | 8/2000 | Wang et al. | 250/288 |
| 7,460,225 B2 * | 12/2008 | Karanassios | 356/316 |
| 8,253,098 B2 * | 8/2012 | Hiraoka et al. | 250/288 |
| 8,519,354 B2 * | 8/2013 | Charipar et al. | 250/423 R |
| 2004/0089802 A1 * | 5/2004 | Kato | 250/285 |
| 2005/0211685 A1 * | 9/2005 | Blankenship | 219/130.4 |
| 2009/0302215 A1 * | 12/2009 | Guna et al. | 250/283 |
| 2011/0042560 A1 * | 2/2011 | Ouyang et al. | 250/282 |
| 2011/0108726 A1 | 5/2011 | Hiraoka et al. | |
| 2012/0292501 A1 * | 11/2012 | Sugiyama et al. | 250/288 |
| 2012/0292526 A1 * | 11/2012 | Hiraoka et al. | 250/423 R |
| 2013/0280819 A1 * | 10/2013 | Cooks et al. | 436/173 |
| 2014/0011202 A1 * | 1/2014 | Jacquet et al. | 435/6.12 |
| 2014/0048699 A1 * | 2/2014 | Ratner et al. | 250/282 |

OTHER PUBLICATIONS

Hiraoka et al., Development of a remote-from-plasma dielectric barrier discharge ion source and its application to explosives, Journal of Mass Spectrometry Society of Japan, vol. 58(6), pp. 215-220, 2010.

Chen et al., Application of probe electrospray ionization for biological sample measurements, Environ. Control Biol., vol. 47(2), pp. 73-86, 2009.

Na et al., Development of a dielectric barrier discharge ion source for ambient mass spectrometry, Annual Conference on Mass Spectrometry, Book of Abstracts Dai 56 Kai, pp. 436-437, 2008.

Na et al., Direct detection of explosives on solid surfaces by mass spectrometry with an ambient ion source based on dielectric barrier discharge, Journal of Mass Spectrometry, vol. 42, pp. 1079-1085, 2007.

Na et al., Development of a dielectric barrier discharge ion source for ambient mass spectrometry, Journal of American Society for Mass Spectrometry, vol. 18, pp. 1859-1862, 2007.

PCT/ISA/220 from PCT/JP2011/053314 dated May 17, 2011.

Written Opinion from PCT/JP2011/053314 dated May 17, 2011.

International Search Report from PCT/JP2011/053314 dated Dec. 2, 2010.

* cited by examiner

IONIZATION APPARATUS AND IONIZATION ANALYSIS APPARATUS

BACKGROUND OF THE INVENTION

1. Field of the Invention

This invention relates to an ionization apparatus and to an ionization analysis apparatus utilizing barrier discharge.

2. Description of the Related Art

Examples of an ionization analysis method and apparatus utilizing barrier discharge are described in the following literature:

Na Na, Chao Zhang, Mengxia Zhao, Sichun Zhang, Chengdui Yang, Xiang Fang and Xinrong Zhang, "Direct detection of explosives on solid surfaces by mass spectrometry with an ambient ion source based on dielectric barrier discharge", J. Mass Spectrom. 2007; 42:1079-1085

Na Na, Mengxia Zhao, Sichun Zhang, Chengdui Yang and Xinrong Zhang, "Development of a Dielectric Barrier Discharge Ion Source for Ambient Mass Spectrometry", J Am Soc Mass Spectrom. 2007, 18, 1859-1862

The ion analysis method and apparatus described in these references have a plate-shaped electrode, a glass plate placed on the surface of the plate-shaped electrode and a needle-shaped electrode disposed substantially perpendicular to the surface of the glass plate (the plate-shaped electrode) and spaced away from the glass plate, and impress an alternating high-voltage across the plate-shaped electrode and needle-shaped electrode and induce a barrier discharge. A sample serving as an object to undergo analysis is placed on the glass plate and is exposed to a plasma torch produced by the barrier discharge. As a result, atoms and molecules are desorbed from the sample and ionized. The ions generated are introduced to a mass analysis apparatus and analyzed.

With the ionization methods described in the above-mentioned literature, ionization of the sample is carried out in a space that is open to the atmosphere. Many of the ions generated, therefore, diffuse into the atmosphere and only some of them are introduced into the mass analyzer. Sensitivity is sacrificed as a result.

SUMMARY OF THE INVENTION

An object of the present invention is to provide an ionization apparatus and an ionization analysis apparatus in which highly sensitive ionization analysis is possible.

Another object of the present invention is to provide an ionization apparatus having a simple structure.

An ionization apparatus according to the present invention comprises: a barrier discharge tube portion; a sample introducing tube portion; an ion supply tube portion; and an ionization chamber wall forming a closed-type ionization chamber. The barrier discharge tube portion has a portion formed by a dielectric and is equipped with an outer electrode and an inner electrode that are disposed respectively on an outer circumferential surface side of and internally of the dielectric portion. The sample introducing tube portion has, at one end thereof, a sample introducing port that leads to the external environment. The ionization chamber, which is cut off from the external environment, is formed forward of the barrier discharge tube portion by enclosing a space, which is directed toward one end of the ion supply tube portion from the other end of the sample introducing tube portion, by the ionization chamber wall. The ion supply tube portion has an ion supply port, which leads to an analysis apparatus, at the other end thereof.

The cross sections of the tubular portions of the barrier discharge tube portion, sample introducing tube portion and ion supply tube portion are not limited to circular cross sections and may just as well be square (inclusive of polygonal), elliptical or of any other shape. "Forward of the barrier discharge tube portion" refers to the direction toward the ionization chamber. A specific example of the sample introducing port of the sample introducing tube portion is a sampling nozzle. The "ion supply port of the ion supply tube portion" corresponds to an ion introducing port as seen from the side of the analysis apparatus.

A discharge gas flows into the barrier discharge tube portion and a high-frequency high voltage is impressed across the outer and inner electrodes thereof, whereby a barrier discharge occurs. As a result, metastable excited species and other ion species are generated and sent to the ionization chamber (plasma does not extend as far as the ionization chamber). On the other hand, a gas containing a gas or particles to be analyzed is introduced into the ionization chamber from the sample introducing tube portion (a case where a gas does not contain a gas or particles to be analyzed also is conceivable). In any case, the gas introduced from the sample introducing tube portion is ionized in the ionization chamber by Penning ionization and reactive ionization, etc. The generated ions are fed to the ion analysis apparatus through the ion supply tube portion and are analyzed.

Since the ionization chamber is a closed space and almost all of the ions generated here are fed to the analysis apparatus through the ion supply tube portion, sensitivity is not sacrificed and analysis is possible at a high sensitivity. In addition, the ionization apparatus is simple in structure.

In one embodiment, the ionization chamber wall has three connection ports and a forward end of the barrier discharge tube portion, the other end of the sample introducing tube portion and the one end of the ion supply tube portion are connected to respective ones of the connection ports. A specific example of the ionization chamber wall is a T-shaped tube body.

In another embodiment, the sample introducing tube portion has a portion made of an electrical conductor, and the portion made of the electrical conductor is inserted into the barrier discharge tube portion as the inner electrode. The barrier discharge tube portion is connected to the ion supply tube portion and the ion supply tube portion serves also as the ionization chamber wall. As a result, the structure is extremely simple.

In a preferred embodiment, the ionization chamber is held in a state in which the pressure thereof is reduced below that of the external environment.

In general, the interior of the analysis apparatus is held in vacuum. If ions are suddenly introduced into the evacuated analysis apparatus from the state of the external environment (atmospheric pressure), there is the possibility that, owing to the large pressure difference, the ions will diffuse broadly and vigorously into the entirety of space in the vicinity of the ion introducing port inside the analysis apparatus. However, when the ions are introduced from the ionization chamber in which pressure has been reduced, they are introduced into the analysis apparatus gently and, due to the reduction in pressure, are capable of being made to converge efficiently by the electric field. The efficiency of ion capture, therefore, is improved. As a result, since many ions are capable of contributing to analysis, ion detection efficiency rises.

There are various methods for holding the interior of the ionization chamber in a reduced-pressure state. As one example, the cross-section area of an opening in the sample introducing tube portion (at the location where the tube is narrowest) is set to be smaller than the cross-section area of an opening in the ion supply tube portion (at the location where the tube is narrowest). So doing makes it possible to evacuate the closed space so as to reduce its pressure to vacuum (reduced-pressure state), which is a pressure lower than atmospheric pressure. The flow rate of the discharge gas that flows into the ionization chamber from the barrier discharge tube portion is adjusted, if it is needed, so that the pressure of the ionization chamber can be held at an appropriate value.

In one embodiment, the ionization chamber wall and the ion supply tube portion are electrically insulated and a DC voltage is impressed across them. The electrodes of the DC voltage are decided in accordance with the polarity of the ions in such a manner that the ions will be introduced by the analysis apparatus in excellent fashion.

The present invention further provides an ionization analysis apparatus having an ionization apparatus and the above-described analysis apparatus.

In one embodiment, the analysis apparatus has in its interior one or a plurality of reduced-pressure chambers leading to the ion supply port. The interior of the ionization chamber is held in a state in which the pressure thereof is reduced below that of the external environment, and the reduced-pressure chamber is held at a pressure lower than that within the ionization chamber. In a case where a plurality of reduced-pressure chambers are provided, they are reduced in pressure in stepwise fashion. As a result, ions progress through evacuated regions that have been reduced in pressure stepwise in two, three or more stages devoid of a large pressure difference and are introduced in the analyzing section of the analysis apparatus very gently.

DESCRIPTION OF THE PREFERRED EMBODIMENT

Figure 1:
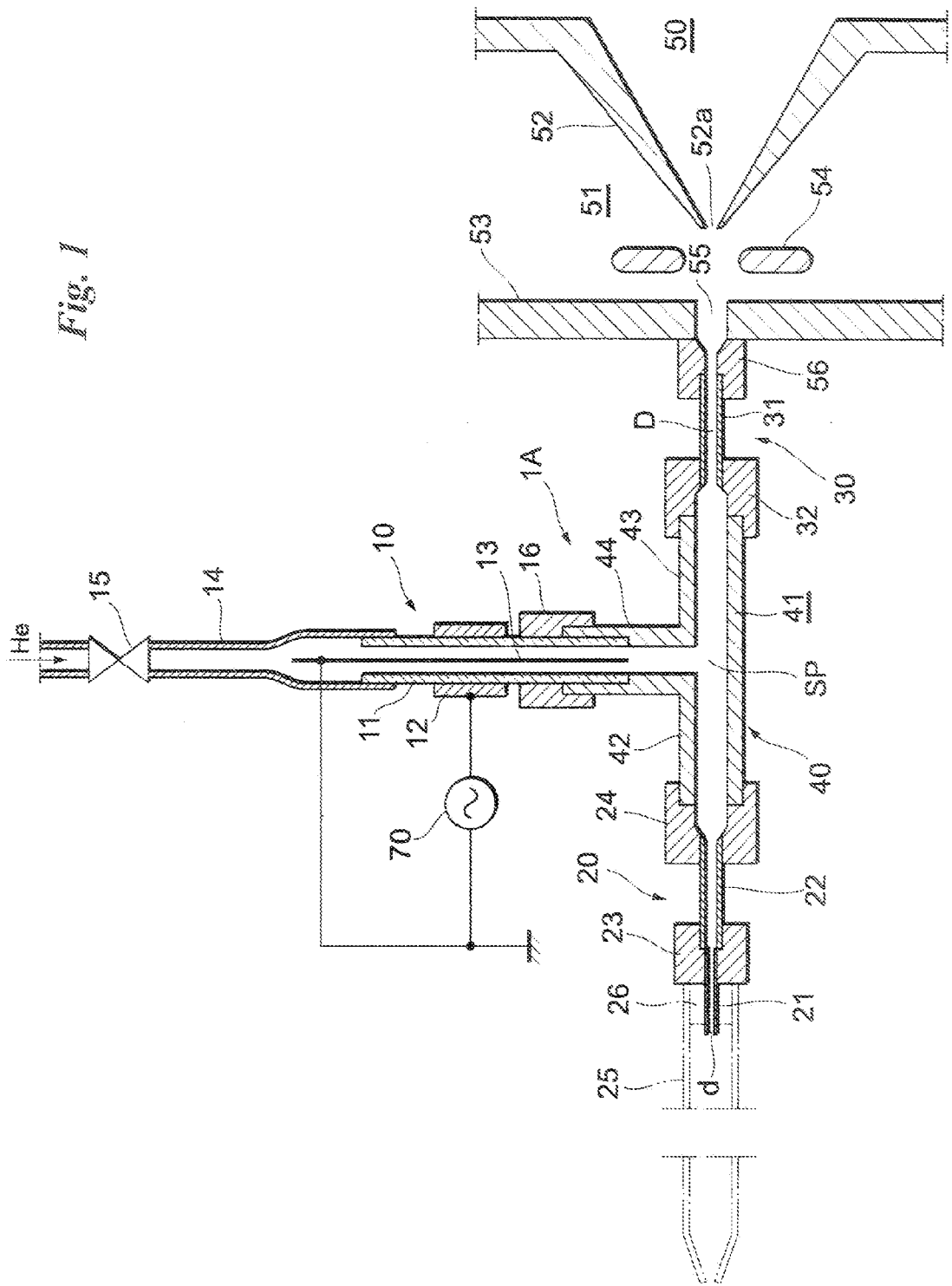
FIG. 1 is a sectional view illustrating an ionization apparatus of a first embodiment together with an analysis apparatus.

FIG. 1 illustrates an ionization apparatus according to a first embodiment together with a mass analysis apparatus.

The combination of an ionization apparatus and a mass analysis apparatus (analysis apparatus) will be referred to as an ionization analysis apparatus.

Mass spectrometers of all types that introduce ions into a vacuum from atmospheric pressure can be used as the mass analysis apparatus, examples being a time-of-flight mass spectrometer, an ion-trap mass spectrometer and a quadrupole mass spectrometer, etc. Since this type of mass analysis apparatus is such that the interior thereof is held at a high vacuum (less than $10^5$ Torr as one example), a large pressure difference exists between the interior and the atmosphere. In general, ions are taken (sucked) into the mass analysis apparatus from the outside utilizing this pressure difference (differential pumping).

A mass analysis apparatus 50 in this embodiment is of the type in which a reduced-pressure chamber 51 is formed forward of a skimmer 52. The reduced-pressure chamber 51 is formed by a flange (a surrounding wall or device wall) (or a portion of the housing of the analysis apparatus 50) 53. The flange 53 has an ion introducing port 55 at a position opposing an ion introducing port 52a of the skimmer 52. A ring lens 54 is provided in the reduced-pressure chamber 51 between the ion introducing ports 55 and 52a. Ions that have been introduced into the reduced-pressure chamber 51 from the ion introducing port 55 are converged by the lens 54 and taken into the high-vacuum mass analysis apparatus 50 through the ion introducing port 52a. The pressure within the reduced-pressure chamber 51 is on the order of 1 Torr, by way of example.

An ionization apparatus 1A is mounted on the front face of the above-mentioned mass analysis apparatus 50. In this embodiment, the ionization apparatus 1A has been mounted on the front face of the flange 53.

In this embodiment, the ionization apparatus 1A has been constructed so as to have a closed ionization chamber that is cut off from the outside (with the exception of a sampling nozzle, barrier discharge tube valve and ion supply port, which will be described later). Specifically, the ionization apparatus 1A is equipped with a T-shape tube (ionization chamber wall) 41. The portion that is the T-shaped tube 41 will be referred to as an ionization chamber portion 40.

The T-shaped tube 41 is formed by joining three tube portions, namely first, second and third tube portions 42, 43 and 44 in such a manner that they communicate with one another. The tube portions 42 and 43 are connected in linear fashion and the tube portion 44 is joined perpendicularly to the joint between the tube portions 42 and 43. The interior space where the tube portions 42, 43 and 44 are joined is an ionization chamber SP. As will be described later, the ionization chamber SP is held in a state of reduced pressure (a state in which pressure is lower than atmospheric pressure and higher than the pressure within the reduced-pressure chamber 51).

If the T-shaped tube 41 is fabricated from metal (an electrical conductor), then a positive or negative DC voltage is applied so that an electrical repulsive force can be produced which will cause ions to travel in the direction of the analysis apparatus 50, as in a second embodiment described later. However, it is unnecessary to limit the tube to a metal, and the tube may be formed from an insulator such as glass.

An intermediate pipe 22 is connected by a coupling (joint) 24 to the end of the first tube portion 42 on the side of the external environment, and a sampling nozzle 21 is connected to the intermediate pipe 22 by a coupling. The tip of the sampling nozzle 21 is a sample introducing port. A ion supply tube 31 is connected by a coupling 32 to the end of the second tube portion 43 that is on the side of the analysis apparatus, and the ion supply tube 31 is joined by a coupling (adapter) 56 to the flange 53 on the outer side of the mass analysis apparatus 50. The end portion of the ion supply tube 31 on the side of the analysis apparatus is an ion supply port and leads to an ion introducing port 55 of flange 53 through a coupling 56. Thus, the sampling nozzle 21 communicates with the ion introducing ports 55 and 52a through the intermediate pipe 22, T-shaped tube 41 and ion supply tube 31. The portion of the sampling nozzle 21 and intermediate pipe 22 will be referred to as a sample introducing portion (sample introducing tube portion) 20 and a portion of the ion supply tube 31 will be referred to as an ion supply portion (ion supply tube portion) 30.

Although the sampling nozzle 21, intermediate pipe 22, ion supply tube 31 and couplings 23, 24, 32 and 56 can all be fabricated from metal, the material is not necessarily limited to metal. For example, besides a metal capillary, it is also possible to use an insulator such as a silica tube as the sampling nozzle.

A barrier discharge tube 11 is connected to the third tube portion 44 by a coupling 16. The barrier discharge tube 11 is made of a dielectric (glass, for example). The tip of the barrier discharge tube 11 does not project as far as the first and second tube portions 42, 43. The outer circumferential surface of the barrier discharge tube 11 is provided with an outer electrode 12, and the interior of the tube 11 is provided with a linear inner electrode 13 along the center thereof (maintaining a gap between itself and the inner surface of the tube 11) (the supporting body of the inner electrode 13 is not shown). Although the position of the tip of inner electrode 13 is substantially the same as the position of the tip of barrier discharge tube 11, it may project outside of the tube 11 or may be somewhat recessed within the tube. The portion constituted by the barrier discharge tube 11 will be referred to as a barrier discharge portion (barrier discharge tube portion) 10.

A discharge gas supply tube 14 is connected to the barrier discharge tube 11 (using a coupling if necessary). The supply tube 14 is provided with a flowrate adjusting valve 15 at a point along the length thereof. The supplied amount (flowrate) of discharge gas (He gas, for example) supplied from a discharge gas tank (bomb) (not shown) or the like (a discharge gas supply source) is adjusted by the valve 15.

A high-frequency high voltage is impressed across the outer electrode 12 and inner electrode 13 in the barrier discharge portion 10 by a high-frequency, high-voltage source 70. As a result, a barrier discharge is generated within the barrier discharge tube 11 and forwardly thereof (in the direction in which the discharge gas flows, i.e., at the side of the T-shaped tube 41). The barrier discharge does not reach the ionization chamber (the interior space at the portion where the three tube portions 42 to 44 are joined) SP. A rare gas such as argon (Ar) or helium (He), nitrogen ($N_2$) gas, oxygen ($O_2$) gas or the atmosphere (air) can be used as the discharge gas.

Metastable excited species of the discharge gas (e.g., He), heated electrons (thermoelectrons) and ion species, etc., are produced by the barrier discharge, and these are sent in the direction of the ionization chamber SP through the tube portion 44 by the flow of discharge gas.

On the other hand, a sample gas is drawn in from the sampling nozzle 21 (the sample gas may include the atmosphere, or may include particles, etc., that have evaporated or been desorbed from a solid or liquid sample, the gas being a gas from a gas chromatograph or another gas to be analyzed) (instances where there is no gas to be analyzed also are possible) and flows into the ionization chamber SP through the intermediate pipe 22 and tube portion 42. These sample gases (atoms, molecules, etc.) are ionized (Penning ionization, reactive ionization) by metastable excited species and ion species, etc., generated by the barrier discharge. In molecules having positive electron affinity, thermoelectrons attach themselves to the molecules and negative ions are produced efficiently. Sample ions thus ionized are introduced by the flow of discharge gas, etc., into the reduced-pressure chamber 51 from the ion introducing port 55 through the tube portion 43 and ion supply tube 31, are introduced into the mass analysis apparatus 50 via the ion introducing port 52a and are subjected to mass analysis.

The ionization apparatus having the construction according to this embodiment has the following two characterizing features:

The first is that the ionization chamber SP is closed off from the external environment with the exception of the sampling nozzle 21, the valve 15 of the barrier discharge portion 10 and the ion supply port of the ion supply tube 31, as mentioned above. Consequently, almost all of the ions (with the exception of those that have lost electric charge due to collision with the device wall and those neutralized by recombination of positive and negative ions) produced in the ionization chamber SP are introduced into the mass analysis apparatus 50. As a result, highly efficient, highly sensitive analysis becomes possible. If a portion or the entirety of the ionization chamber SP were to be open to the atmosphere, the ions would diffuse into the atmosphere and ions introduced into the analysis apparatus 50 would become very small in quantity. The above-mentioned problem is solved by the structure of the closed ionization chamber SP and ion supply tube 31.

The second is that since the interior of the ionization chamber SP has been reduced in pressure, the ions generated in the ionization chamber SP are introduced gently into the high-vacuum analysis apparatus 50. In this embodiment, since the reduced-pressure chamber 51 is a stage ahead of the mass analysis apparatus 50 and the pressure thereof is held at a value between the pressure within the ionization chamber SP and the pressure within the analysis apparatus 50, the pressure is successively reduced from the ionization chamber SP and then reaches the interior of the analysis apparatus 50. Accordingly, many of the ions are made available for analysis within the analysis apparatus 50 in reliable fashion. For example, if ions were to be drawn suddenly into the high-vacuum analysis apparatus from the environment at atmospheric pressure, there is a possibility that the ions would diffuse in the interior of the analysis apparatus owing to the large pressure difference. However, such an event is prevented from occurring by the stage-like reduced-pressure structure described above.

Adjustment of the pressure inside the ionization chamber SP is carried out as follows, by way of example: Inner diameter (inner diameter where it is smallest) d of the tip portion (sample introducing port) of the sampling nozzle 21 is set to be smaller than inner diameter D of the ion supply port of ion supply tube 31 (namely the inner diameter where it is smallest in the passageway from the ion supply tube 31 to the ion introducing port 55 of flange 53) (d=0.2 mm, D=0.8 mm, by way of example). That is, the flowrate of the gas drawn into the analysis apparatus 50 can be made larger than the flowrate of the gas that flows into through the nozzle 21. Meanwhile, the discharge gas flows into the ionization chamber SP from the barrier discharge tube 11. Accordingly, by adjusting the above-mentioned diameters d, D, the flowrate of the discharge gas regulated by the valve 15 and the capability of the vacuum pump that evacuates the interior of the analysis apparatus, the interior of the ionization chamber SP can be held in a given reduced-pressure state (e.g., on the order of 10 to 500 Torr including 10 to 100 Torr). Thus, a pressure adjustment in the two stages composed of the ionization chamber SP and reduced-pressure chamber 51 is carried out. The upshot is that the constrictions on the inflow and outflow sides of the ionization chamber are set appropriately and the flowrate of the discharge gas is adjusted by the valve 15.

If an extension pipe 25 is connected to the sampling nozzle 21 via a spacer 26 or directly to the intermediate pipe 22 or tube portion 42 using couplings 23, 24, the spatial zone for collecting the gas to be analyzed is broadened. The extension pipe 25 may be made long (e.g., 1 m or more). A flexible tube can also be adopted as the extension pipe 25. The sampling nozzle may be provided at the tip of the extension pipe 25 or may be provided close to the ionization chamber SP as illustrated.

Figure 2:
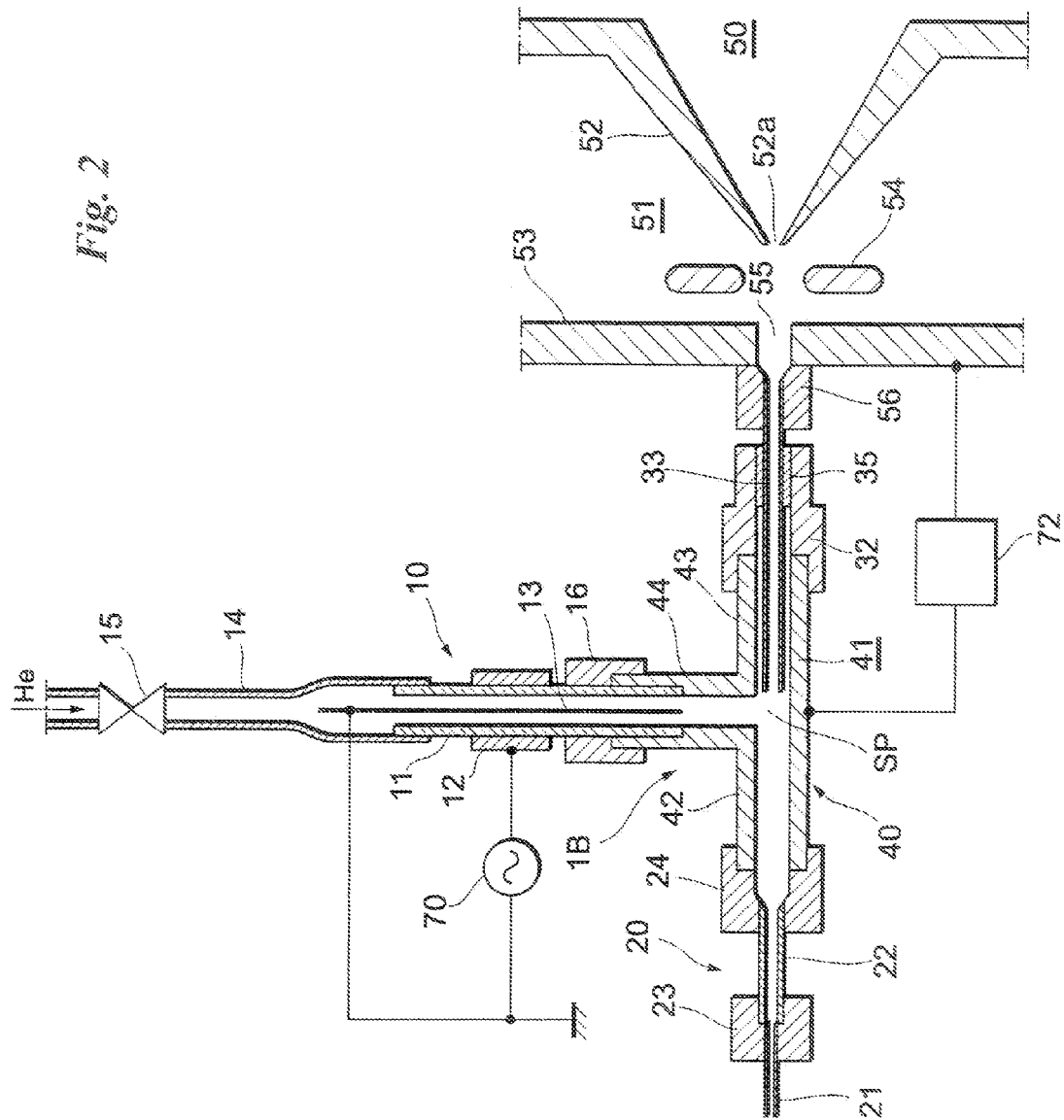
FIG. 2 is a sectional view illustrating an ionization apparatus of a second embodiment together with an analysis apparatus.

FIG. 2 illustrates another embodiment. In order to introduce ions directly into the analysis apparatus 50 from the ionization chamber SP in ionization apparatus 1B, an extension tube (ion supply tube) 33 is extended from the portion of a coupling 56 of flange 53 up to the ionization chamber SP. Further, a DC voltage is impressed across the analysis apparatus 50 (or its outer wall or flange 53) and the T-shaped tube (ionization chamber wall) 41 by a DC power supply 72. To achieve this, an insulator 35 is interposed between coupling 32, which connects the tube portion 43 of the T-shaped tube 41 to the extension tube 33 at a point along its length, and the extension tube 33, thereby electrically insulating the T-shaped tube 41 and extension tube 33. The coupling 32 may be formed from an insulator. The extension tube 33 and coupling 56 are made of metal and are at the same electrical potential as that of the flange 53.

The polarity of the voltage applied to the T-shaped tube 41 is changed in accordance with the polarity of the ions generated inside the ionization chamber SP. A positive potential is applied in case of positive ions and a negative potential in case of negative ions. Preferably, a potential difference is similarly impressed also across the flange 53 and skimmer 52.

Other arrangement is the same as those shown in FIG. 1, and components identical with those shown in FIG. 1 are designated by like reference characters to avoid a redundant description.

Figure 3:
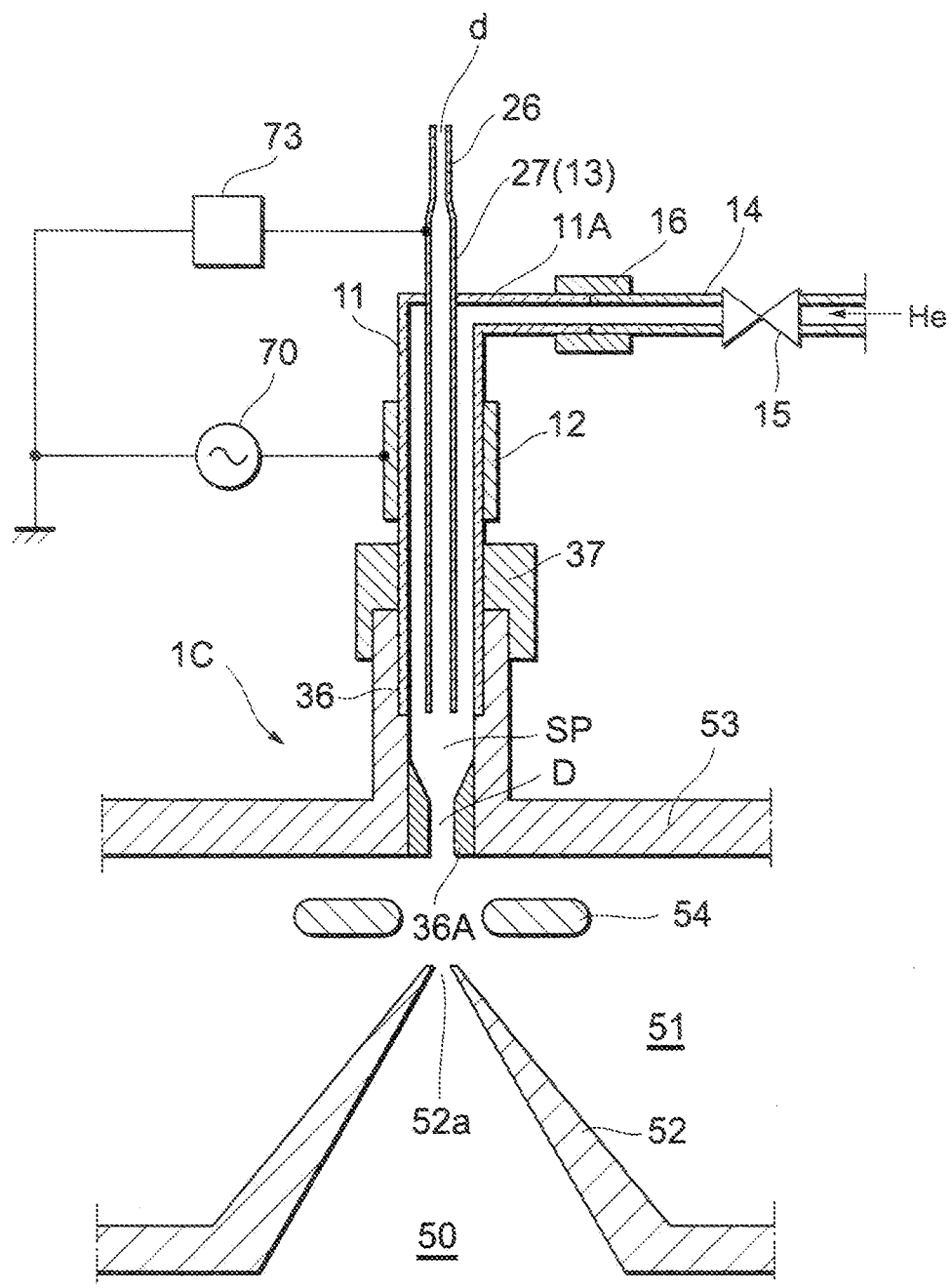
FIG. 3 is a sectional view illustrating an ionization apparatus of a third embodiment together with an analysis apparatus.

FIG. 3 illustrates a further embodiment.

An ionization apparatus 1C does not use a T-shaped tube and is provided with an ion supply tube (ion introducing tube) 36 directly [or by a coupling (adapter), not shown] so as to surround the ion introducing port in flange 53 of the analysis apparatus 50, and the interior thereof defines the ionization chamber SP. The ion supply port of the ion supply tube 36 and the ion introducing tube of the flange 53 are shared and the inner diameter D of this portion is adjusted by inserting a ring 36A or the like.

The barrier discharge tube 11 is mounted on the ion supply tube 36 by a coupling 37 and the interior of the barrier discharge tube 11 communicates with the interior of the ion supply tube 36. The ionization chamber SP is forward of the barrier discharge tube 11.

A sample introducing tube 27 having a sampling nozzle 26 is formed from a metal, is inserted into the center portion of the barrier discharge tube 11 while maintaining a hermetic state and serves also as the inner electrode 13. The position of the end portion of the sample introducing tube 27 on the side of the analysis apparatus substantially coincides with the position of corresponding end portion of the barrier discharge tube 11 (either end portion may extend slightly beyond the other). As a matter of course, there is a gap between the inner surface of the barrier discharge tube 11 and the sample introducing tube 27. The barrier discharge tube 11 is bent at a point along its length and is connected to the discharge gas supply tube 14 via the coupling 16.

A high-frequency high voltage is impressed across the inner electrode (sample introducing tube) 27 (13) and outer electrode 12 of the barrier discharge tube 11 by power supply 70 and a DC voltage is applied by being superimposed upon this voltage by a DC power supply 73 in accordance with the polarity of the ions generated. Other arrangement is identical with those shown in FIG. 1.

In this embodiment as well, owing to metastable excited species and the like generated by the barrier discharge (the barrier discharge does not extend as far as the ionization chamber SP), the sample that has been introduced by the sample introducing tube 27 is ionized by an ionization process such as Penning ionization and is introduced into the analysis apparatus 50. The ionization chamber SP is held in a state of suitable pressure reduction.

Although the analysis apparatus 50 is provided with the reduced-pressure chamber 51 in the foregoing embodiments, the reduced-pressure chamber 51 need not necessarily be provided.

Figure 4:
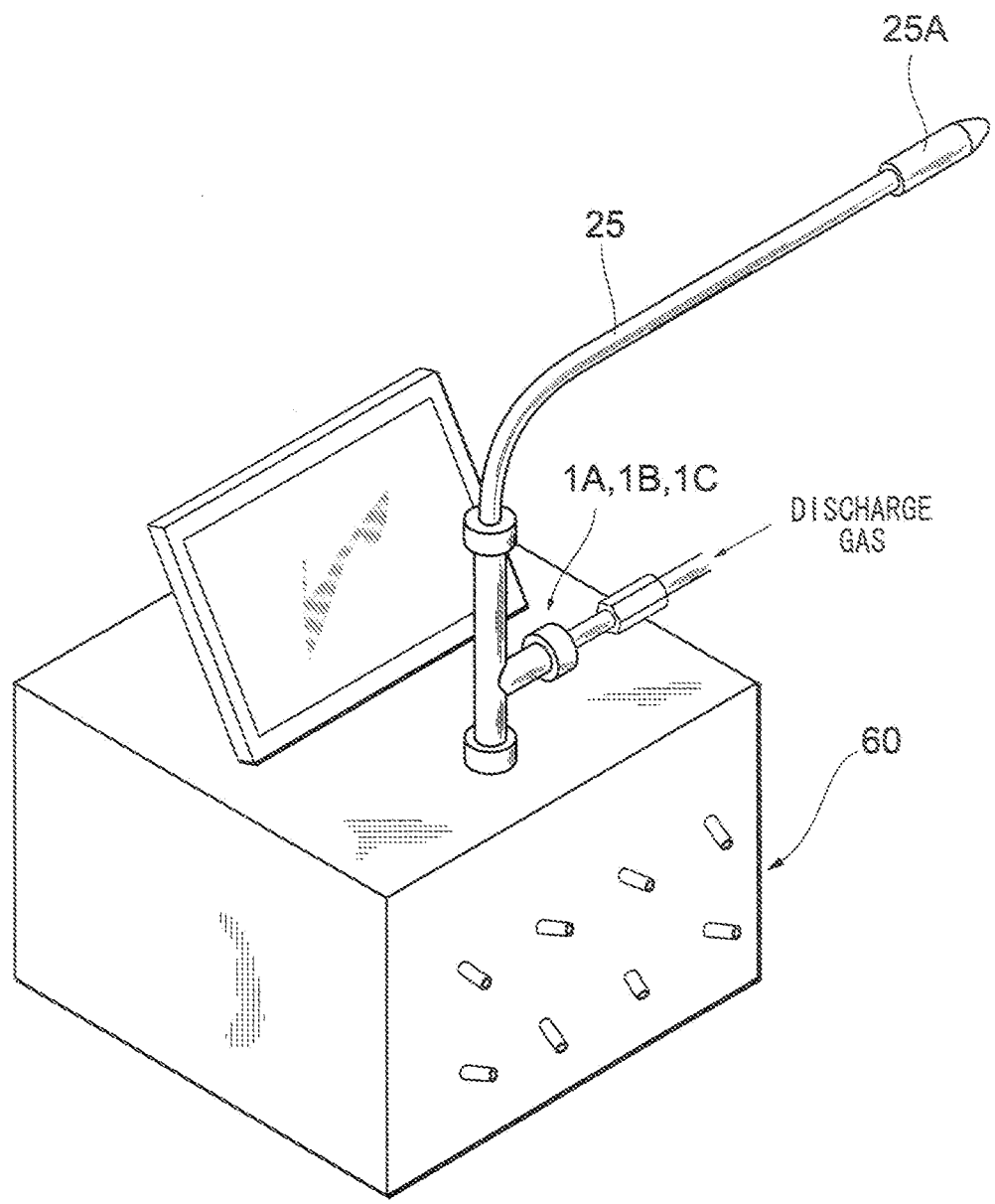
FIG. 4 is a perspective view illustrating a portable-type ionization analysis apparatus.

FIG. 4 illustrates a portable-type ionization analysis apparatus. An ionization analysis apparatus 60 includes the housing of a small-size mass analysis apparatus and the necessary control panel and display device, which are provided on the housing, as well the above-described ionization apparatus 1A (or 1B or 1C) attached thereto. The extension pipe 25, which is flexible and has a sampling nozzle 25A, is connected to an ion introducing tube portion.

Figure 5:
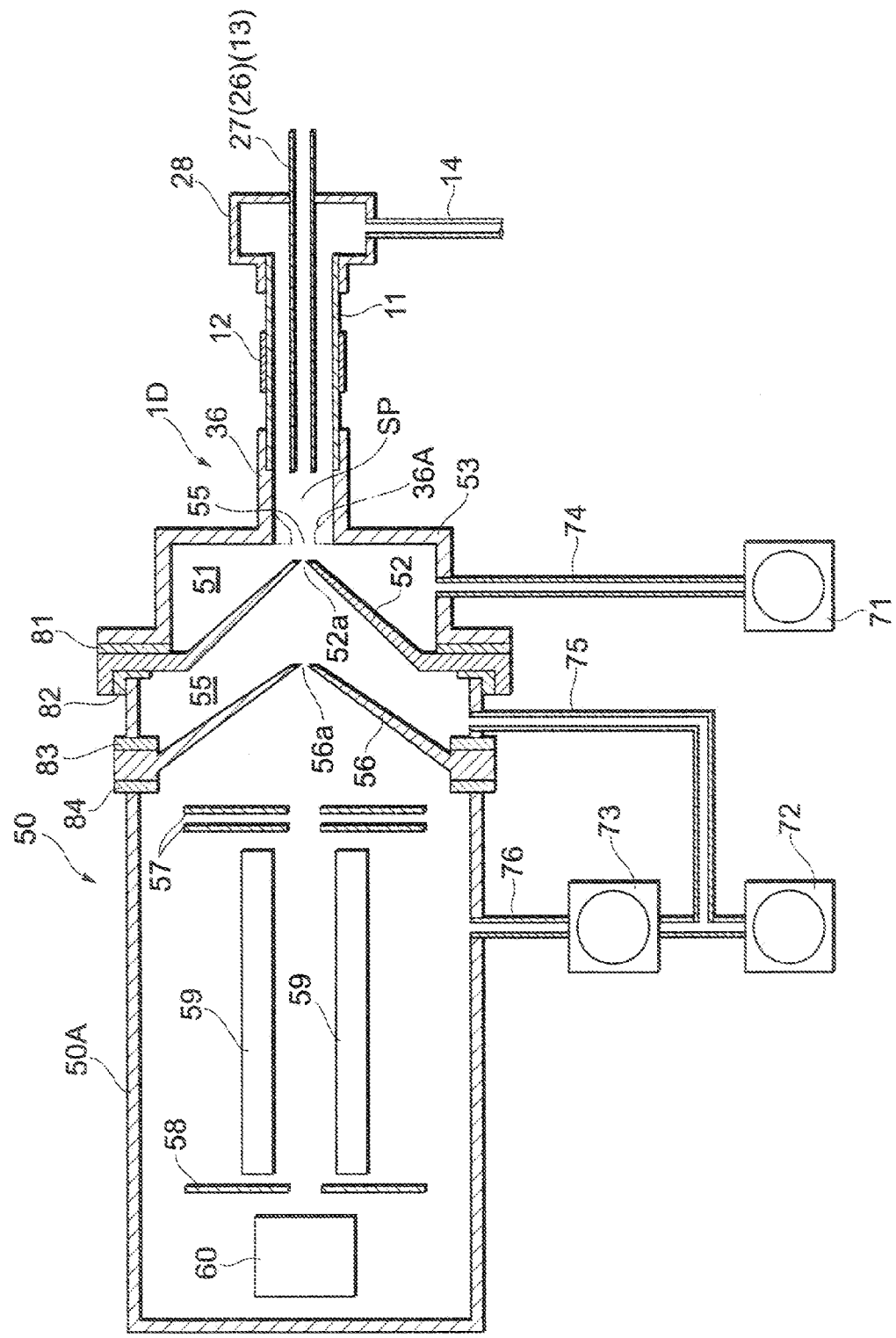
FIG. 5 is a sectional view illustrating an ionization apparatus of a fourth embodiment together with an analysis apparatus.

FIG. 5 illustrates another embodiment in which a mass analysis apparatus is provided with a reduced-pressure structure in stepwise fashion. In this embodiment as well, components identical with those in the already described embodiments are designated by like reference characters to avoid a redundant description as much as possible.

A quadrupole mass spectrometer is illustrated as the mass analysis apparatus 50. The ion-supply side of the mass analysis apparatus 50 is provided with the reduced-pressure chamber (first reduced-pressure chamber) 51 using the above-mentioned flange (surrounding wall or device wall) 53. This can also be expressed as stating that the first reduced-pressure chamber 51 is partitioned by providing the skimmer 52 on the ion-supply side of housing 50A of the analysis apparatus 50. One additional skimmer 56 is provided farther within the interior of the apparatus than the skimmer 52 (namely on the side opposite the ion-supply side) with a clearance defined between it and the skimmer 52. A second reduced-pressure chamber 55 is formed between the skimmers 52 and 56. A small ion introducing port 56a is provided in the skimmer 56.

A ring lens 57, four rod electrodes 59, a ring lens 58 and an ion detector 60, etc., are disposed in the interior of the analysis apparatus 50.

A diaphragm pump 71 is connected to the first reduced-pressure chamber 51 by an exhaust pipe 74, and the first reduced-pressure chamber is reduced in pressure to 100 to 200 Torr, by way of example.

The second reduced-pressure chamber 55 is evacuated by a rotary pump 72 connected by an exhaust pipe 75 and is reducing in pressure to, e.g., several Torr.

The interior of the main body of the quadrupole mass spectrometer in which the four rod electrodes have been placed is evacuated to a high vacuum of $10^{-5}$ Torr by a turbomolecular pump, for example, through an exhaust pipe 76.

Since it is thus arranged so that pressure is reduced in three stages within the analysis apparatus 50, ions can be prevented from diffusing inside the analysis apparatus 50.

In ionization apparatus 1D the barrier discharge tube 11, which is made of a dielectric, is connected to the ion supply tube 36 provided on the flange 53, and the tip of the barrier discharge tube 11 is closed by a connection portion 28. The sample introducing tube 27 (which serves also as the sampling nozzle 26 and as the inner electrode 13) is inserted into the interior of the barrier discharge tube 11 through the connection portion 28. The discharge gas supply tube 14 is connected to the connection portion 28.

In a manner the same as that of the embodiment shown in FIG. 3, a high-frequency high voltage is applied across the inner electrode 13 and outer electrode 12 (this application of voltage is not shown). If necessary, a DC voltage is impressed across these electrodes in accordance with the polarity of the ions. If necessary, the skimmers 52, 56 are electrically insulated from housing 50A of the analysis apparatus by insulators 81, 82, 83, 84, and a DC voltage for facilitating the introduction of ions into the interior of the apparatus should also be applied to the skimmers 52, 56. Furthermore, if the ring 36A is provided at the ion introducing port 55, as indicated by the phantom lines, and the pressure in the ionization chamber SP is made different from that in the reduced-pressure chamber 51, then the structure obtained is one in which pressure is reduced in four stages overall.

When a quadrupole mass spectrometer is used as the mass analysis apparatus, a size reduction is possible and it is possible for the ionization analysis apparatus shown in FIG. 5 to be constructed as an apparatus of the portable type as shown in FIG. 4.

Figure 6:
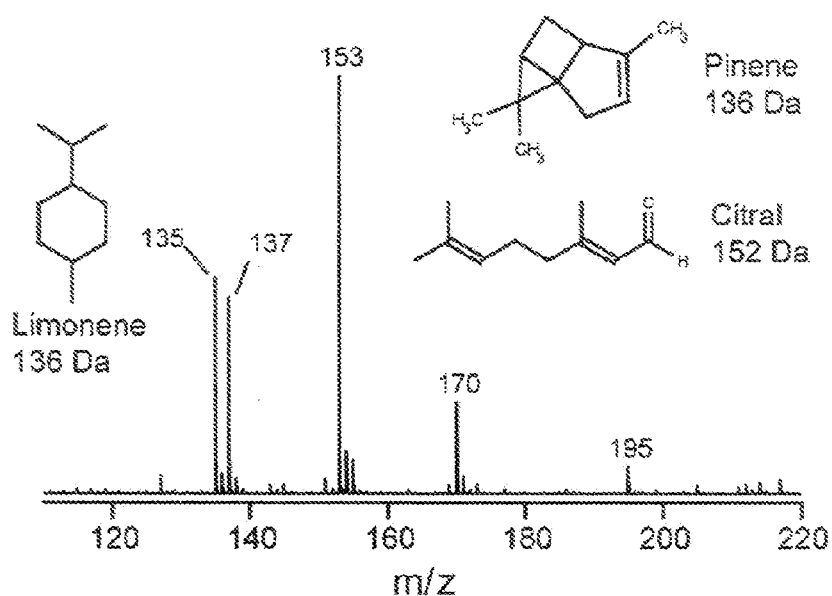
FIG. 6 is a mass spectrum illustrating result of analyzing a lemon.
Figure 7:
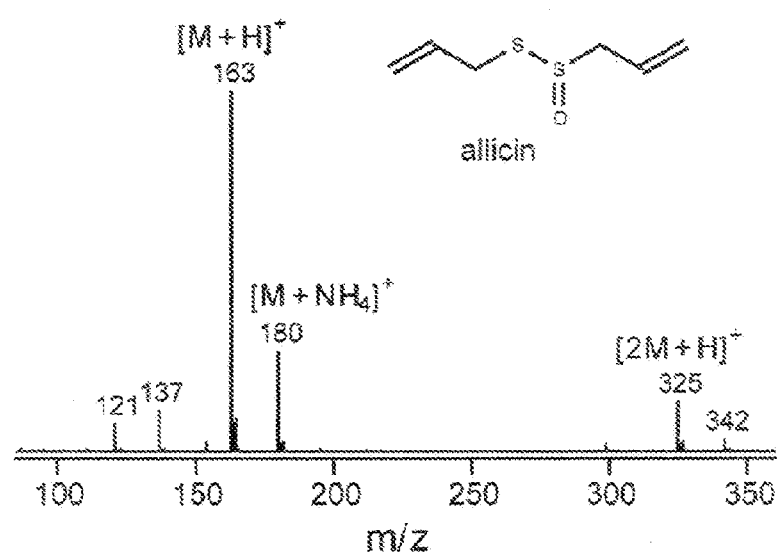
FIG. 7 is a mass spectrum illustrating result of analyzing garlic.
Figure 8:
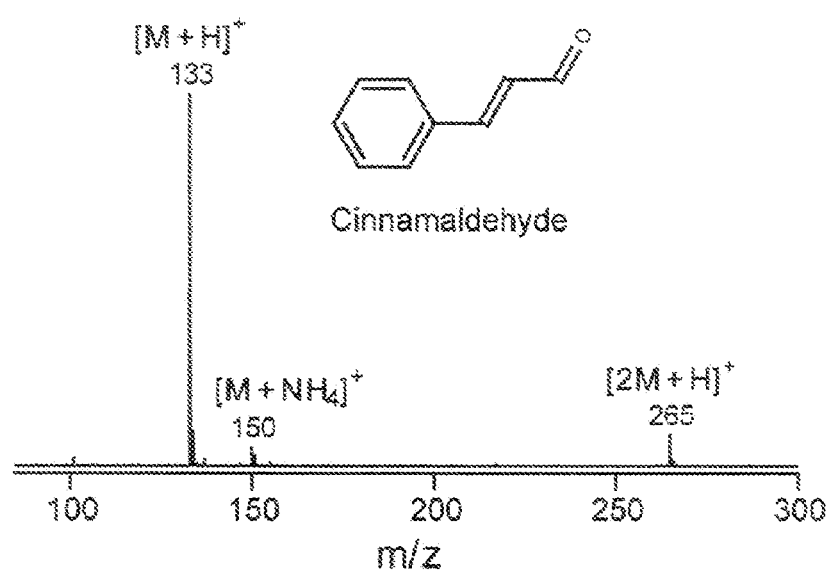
FIG. 8 is a mass spectrum illustrating result of analyzing cinnamon (powdered)

FIGS. 6, 7 and 8 illustrate mass spectrums obtained when lemon, garlic and cinnamon (powdered), respectively, were brought close to the tip of the sampling nozzle 21 in the ion analysis apparatus shown in FIG. 1.

FIGS. 9 to 13 illustrates analytical results using the ionization analysis apparatus shown in FIG. 1.

Figure 9:
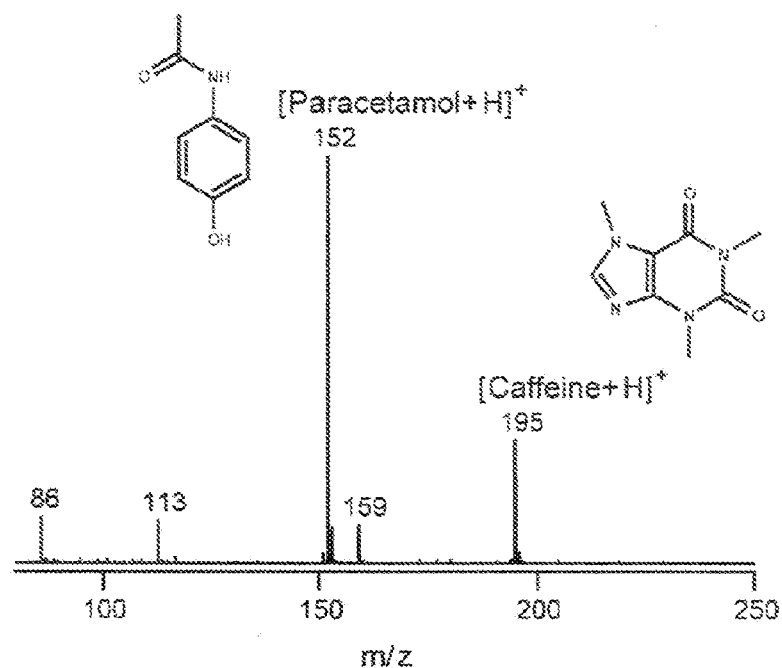
FIG. 9 is a mass spectrum illustrating result of analyzing a medicinal cold tablet.

FIG. 9 is an example of direct analysis of a medicinal cold tablet. The sample molecules are ionized softly with almost no production of fragment ions. This is a characteristic of He* Penning ionization.

Figure 10:
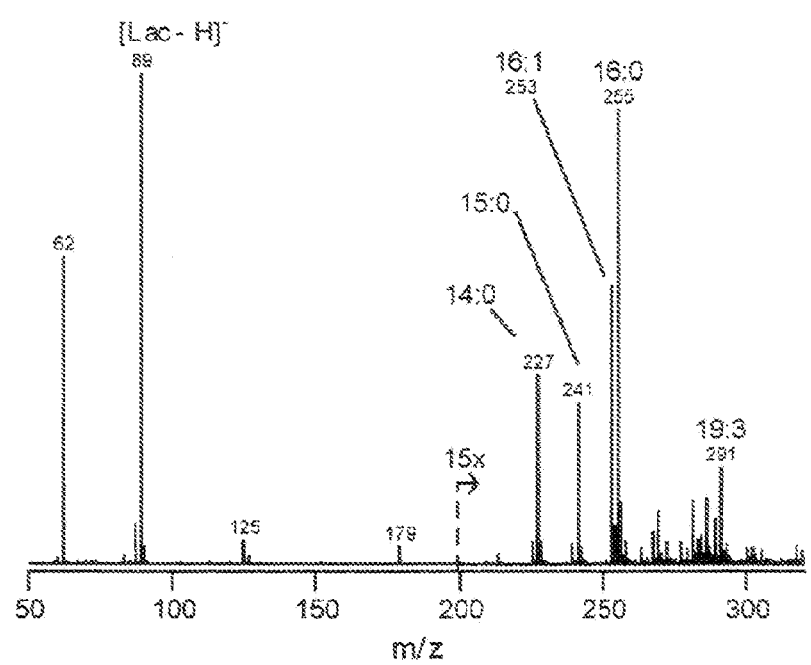
FIG. 10 is a mass spectrum illustrating result of analyzing a fingerprint (a deposit)

FIG. 10 is an example in which a finger was pressed against aluminum foil to leave a fingerprint (a deposit) and the aluminum foil was brought close to the sampling nozzle 21 and was heated from the back side by spraying it with heated nitrogen to thereby cause vaporization, followed by analyzing the vapor components. Measurement was in the negative-ion mode. Negative ions of lactic acid, fatty acids and the like were strongly observed.

Figure 11:
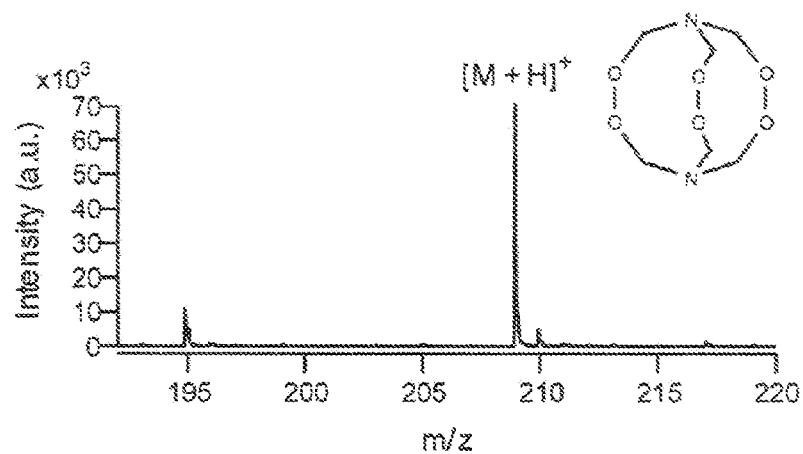
FIG. 11 is a mass spectrum illustrating result of analyzing HMTD 10 ng.
Figure 12:
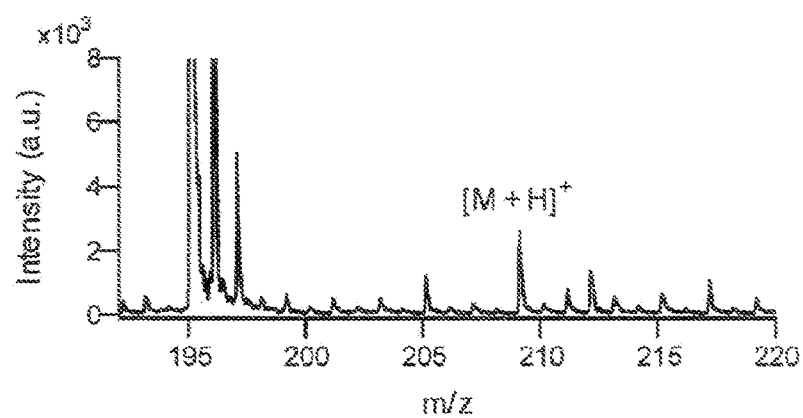
FIG. 12 is a mass spectrum illustrating result of analyzing HMTD 5 pg.
Figure 13:
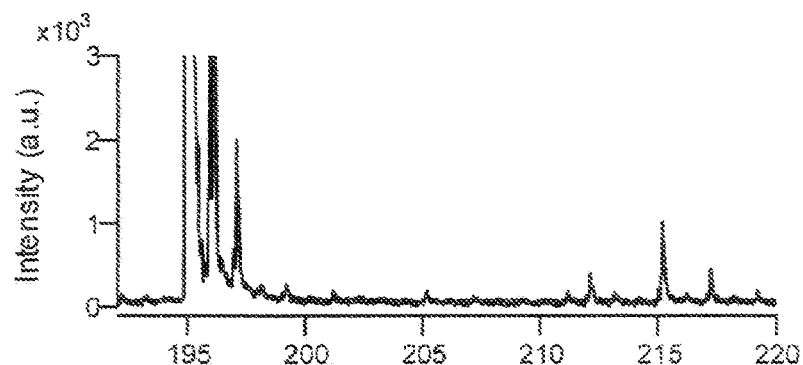
FIG. 13 is a mass spectrum of a blank.

FIGS. 11 and 12 are examples of analysis of HMTD (Hexamethylenetriperoxidediamine) (N(CH$_2$—O—O—CH$_2$)$_3$ N), which is a hand-made explosive. A glass rod was coated with a fixed amount of HMTD, the rod was brought close to the sampling nozzle 21 and was heated from the back side by spraying it with heated nitrogen gas (150° C.) to thereby cause vaporization, followed by analyzing the vapor. FIG. 11 is the case for 10 ng of HMTD and FIG. 12 the case for 5 pg of HMTD. HMTD was detected up to 5 pg. This limit on detection is a value close to the limit of detection sensitivity by a chemical ionization method (gas-phase ion molecule reaction). This confirms the superiority of the present invention. FIG. 13 is a mass spectrum obtained in the case of a blank.

The method of sampling a sample using a sampling nozzle has very broad application as in the foregoing embodiments. For example, if the sampling nozzle is brought close to the laser-irradiated portion in matrix-assisted laser desorption ionization, highly sensitive ion analysis of atmospheric-pressure MALDI is possible. In addition, the method can be used in analysis of vapors produced by laser heating and electrical resistive heating, analysis of foodstuff vapors, analysis of soil, analysis of narcotics, analysis of illegal medicines and analysis of urine, etc. Furthermore, the method can be used in analysis of environmental hormones (PCB, plastics, etc.) contained in dried blood, in fingerprint analysis, analysis of vapors produced from plants, and analysis of exhalations.

The above-described ionization analysis apparatus can be used in combination with probe electrospray in which a probe is made to pierce a sample (all forms of samples that include water content in particular) to collect the sample at the tip of the probe, and a high voltage is applied to the probe to cause desorption and ionization. Ions produced by probe electrospray and neutral gases are sampled by the above-described sampling nozzle and the neutral gases are ionized by Penning ionization within the ionization apparatus. As a result, neutral gas components can also be ionized and detected at the same time as the ions produced by probe electrospray. Generally, with electrospray, polar molecules are readily detected (compounds containing nitrogen or oxygen) and nonpolar molecules (hydrocarbon components, etc.) are difficult to ionize. Since the method of the foregoing embodiments can ionize gas components exhibiting little polarity, the method is a revolutionary one capable of eliminating the intrinsic drawbacks of electrospray.

Furthermore, the apparatus of the foregoing embodiments is applicable to detection of hydrogen peroxide ($H_2O_2$). Specifically, metastable excited species He* having a high energy are formed by barrier discharge in which helium (He) is passed as the discharge gas, atmospheric component gases ($N_2$, $O_2$, etc.) are excited and ionized as a result, and electrons are emitted. The electrons produced attach themselves to oxygen molecules $O_2$ and oxygen-molecule negative ions $O_2^-$ are generated. These oxygen-molecule negative ions $O_2^-$ flow into the ionization chamber SP.

On the other hand, if a gas sampled by the sampling nozzle 21 contains hydrogen peroxide $H_2O_2$, the hydrogen peroxide also is sent to the ionization chamber SP. Oxygen-molecule negative ions $O_2^-$ form strong bonds with the hydrogen peroxide ($H_2O_2$) in the ionization chamber SP and cluster ions $O_2^-$ ($H_2O_2$) of oxygen-molecule negative ions and hydrogen peroxide are produced. The cluster ions are introduced into the mass analysis apparatus 50 from the ion introducing ports 55, 52a (56a) and are detected. That is, the existence and amount of hydrogen peroxide $H_2O_2$ can be detected as cluster ions $O_2^-$ ($H_2O_2$) with oxygen-molecule negative ions.

What is claimed is:

1. An ionization apparatus comprising:
a barrier discharge tube portion; a sample introducing tube portion; an ion supply tube portion; and an ionization chamber comprising an ionization chamber wall;
wherein said barrier discharge tube portion has a portion formed by a dielectric material and is equipped with an outer electrode and an inner electrode that are disposed respectively on an outer circumferential surface side of and internally of the dielectric portion;
said sample introducing tube portion contains a sample introducing port that leads to the external environment;
said ionization chamber is a closed space, wherein the ionization chamber is located forward of said barrier discharge tube portion and is directed toward one end of the ion supply tube portion from the other end of said sample introducing tube portion, by said ionization chamber wall; and
said ion supply tube portion has an ion supply port, which leads to the analysis apparatus, at the other end thereof.

2. An ionization apparatus according to claim 1, wherein said ionization chamber is held in a state in which the pressure thereof is reduced below that of the external environment.

3. An ionization apparatus according to claim 2, wherein cross-section area of an opening in said sample introducing tube portion is smaller than cross-section area of an opening in said ion supply tube portion.

4. An ionization apparatus according to claim 1, wherein said ionization chamber wall has three connection ports and a forward end of said barrier discharge tube portion, said other end of said sample introducing tube portion and said one end of said ion supply tube portion are connected to respective ones of connection ports.

5. An ionization apparatus according to claim 2, wherein said ionization chamber wall has three connection ports and a forward end of said barrier discharge tube portion, said other end of said sample introducing tube portion and said one end of said ion supply tube portion are connected to respective ones of connection ports.

6. An ionization apparatus according to claim 4, wherein said ionization chamber wall is a T-shaped tube body.

7. An ionization apparatus according to claim 1, wherein said ionization chamber wall and said ion supply tube portion are electrically insulated and a DC voltage is impressed across them.

8. An ionization apparatus according to claim 4, wherein said ionization chamber wall and said ion supply tube portion are electrically insulated and a DC voltage is impressed across them.

9. An ionization apparatus according to claim 1, wherein said sample introducing tube portion has a portion made of an electrical conductor, and the portion made of the electrical conductor is inserted into said barrier discharge tube portion as said inner electrode.

10. An ionization apparatus according to claim 2, wherein said sample introducing tube portion has a portion made of an electrical conductor, and the portion made of the electrical conductor is inserted into said barrier discharge tube portion as said inner electrode.

11. An ionization apparatus according to claim 9, wherein said barrier discharge tube portion is connected to said ion supply tube portion and said ion supply tube portion serves also as said ionization chamber wall.

12. An ionization analysis apparatus comprising the ionization apparatus, which is set forth in claim 1, and said analysis apparatus.

13. An ionization analysis apparatus comprising the ionization apparatus, which is set forth in claim 4, and said analysis apparatus.

14. An ionization analysis apparatus comprising the ionization apparatus, which is set forth in claim 9, and said analysis apparatus.

15. An ionization analysis apparatus according to claim 12, wherein said analysis apparatus has a reduced-pressure chamber leading to said ion supply port, the interior of said ionization chamber is held in a state in which the pressure thereof is reduced below that of the external environment, and said reduced-pressure chamber is held at a pressure lower than that within said ionization chamber.

16. An ionization analysis apparatus according to claim 15, wherein said analysis apparatus has at least two stages of reduced-pressure chambers for reducing pressure successively in stepwise fashion.

17. An ionization analysis apparatus according to claim 13, wherein said analysis apparatus has a reduced-pressure chamber leading to said ion supply port, the interior of said ionization chamber is held in a state in which the pressure thereof is reduced below that of the external environment, and said reduced-pressure chamber is held at a pressure lower than that within said ionization chamber.

18. An ionization analysis apparatus according to claim 14, wherein said analysis apparatus has a reduced-pressure chamber leading to said ion supply port, the interior of said ionization chamber is held in a state in which the pressure thereof is reduced below that of the external environment, and said reduced-pressure chamber is held at a pressure lower than that within said ionization chamber.

19. An ionization apparatus according to claim 1, wherein said ionization chamber is held at pressure between 10 to 500 Torr.

20. An ionization apparatus according to claim 1, wherein said ionization chamber is held at pressure between 10 to 100 Torr.

* * * * *